(12) United States Patent
Conrad-Vlasak et al.

(10) Patent No.: US 9,572,942 B2
(45) Date of Patent: Feb. 21, 2017

(54) MEDICAL DRESSING COMPRISING AN APERTURED HYDROGEL

(75) Inventors: Deena M. Conrad-Vlasak, Stillwater, MN (US); Steven B. Heinecke, New Richmond, WI (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 82 days.

(21) Appl. No.: 13/995,232

(22) PCT Filed: Dec. 28, 2011

(86) PCT No.: PCT/US2011/067538
§ 371 (c)(1),
(2), (4) Date: Jun. 18, 2013

(87) PCT Pub. No.: WO2012/092343
PCT Pub. Date: Jul. 5, 2012

(65) Prior Publication Data
US 2013/0274667 A1    Oct. 17, 2013

Related U.S. Application Data

(60) Provisional application No. 61/427,990, filed on Dec. 29, 2010.

(51) Int. Cl.
*A61F 13/02* (2006.01)
*A61M 5/46* (2006.01)
(Continued)

(52) U.S. Cl.
CPC ............. *A61M 5/46* (2013.01); *A61F 13/00* (2013.01); *A61F 13/0203* (2013.01);
(Continued)

(58) Field of Classification Search
CPC .. A61F 13/02; A61F 13/0203; A61F 13/0213; A61F 13/0259; A61F 2013/00748; A61F 2013/00523; A61F 2013/00676; A61F 13/0263; A61F 13/0266; C09J 7/0225; C09J 7/0232; C09J 7/0235
(Continued)

(56) References Cited

U.S. PATENT DOCUMENTS

RE24,906 E    12/1960   Ulrich
3,389,827 A    6/1968   Abere
(Continued)

FOREIGN PATENT DOCUMENTS

GB    2202150    9/1988
GB    2387331    10/2003
(Continued)

OTHER PUBLICATIONS

International Search Report for PCT/US2011/067538, mailed on Aug. 21, 2012, 16 pages.

*Primary Examiner* — Kari Petrik
(74) *Attorney, Agent, or Firm* — 3M Innovative Properties Company; Lynn R. Hunsberger (57) ABSTRACT

Disclosed is an apertured hydrogel that is used in connection with an insertion device to provide comfort at the site of entry into the skin. In one embodiment, the hydrogel contains antimicrobial properties to help inhibit microbial growth at the site of insertion of the device into the skin. In the invention the apertured hydrogel is provided with a medical dressing and comprises a hydrogel having an upper surface and a lower surface, a film covering the upper surface of the hydrogel, a base sheet releasably covering to the lower surface of the hydrogel, an aperture in the film and hydrogel from the upper surface to the lower surface of the hydrogel, wherein the base sheet extends beyond the hydrogel to form a tab.

7 Claims, 3 Drawing Sheets

(51) Int. Cl.
*A61F 13/00* (2006.01)
*A61M 5/158* (2006.01)
*A61M 5/42* (2006.01)
*B32B 3/26* (2006.01)

(52) U.S. Cl.
CPC ........ *A61F 13/025* (2013.01); *A61F 13/0213* (2013.01); *A61F 13/0226* (2013.01); *A61M 5/158* (2013.01); *A61M 5/42* (2013.01); *A61M 5/422* (2013.01); *B32B 3/266* (2013.01); *A61F 2013/00417* (2013.01); *A61F 2013/00748* (2013.01); *Y10T 428/24273* (2015.01); *Y10T 428/24322* (2015.01); *Y10T 428/24331* (2015.01)

(58) Field of Classification Search
USPC .......................................................... 602/57
See application file for complete search history.

(56) References Cited

U.S. PATENT DOCUMENTS

| | | |
|---|---|---|
| 3,645,835 A | 2/1972 | Hodgson |
| 4,112,213 A | 9/1978 | Waldman |
| 4,310,509 A | 1/1982 | Berglund |
| 4,323,557 A | 4/1982 | Rosso |
| 4,472,480 A | 9/1984 | Olson |
| 4,595,001 A | 6/1986 | Potter |
| 4,737,410 A | 4/1988 | Kantner |
| 5,112,618 A * | 5/1992 | Cartmell ............. A61F 13/0203 424/443 |
| 5,160,315 A | 11/1992 | Heinecke |
| 5,447,492 A * | 9/1995 | Cartmell ............. A61F 13/0203 602/41 |
| 5,554,106 A | 9/1996 | Layman-Spillar |
| 5,833,665 A * | 11/1998 | Bootman ................ A61L 15/46 424/443 |
| 2004/0247654 A1 | 12/2004 | Asmus |
| 2004/0247655 A1 | 12/2004 | Asmus |
| 2007/0049859 A1 | 3/2007 | Propp |
| 2008/0132821 A1 | 6/2008 | Propp |
| 2008/0233348 A1 | 9/2008 | Ishiwatari |
| 2011/0098622 A1* | 4/2011 | Hatanaka ........... A61F 13/0269 602/52 |
| 2012/0059300 A1 | 3/2012 | Ovington |

FOREIGN PATENT DOCUMENTS

| | | |
|---|---|---|
| WO | WO 2005/051259 | 6/2005 |
| WO | WO 2009-075636 | 6/2009 |
| WO | WO 2010-056541 | 5/2010 |
| WO | WO 2010-056543 | 5/2010 |

* cited by examiner

MEDICAL DRESSING COMPRISING AN APERTURED HYDROGEL

CROSS REFERENCE TO RELATED APPLICATIONS

This application is a national stage filing under 35 U.S.C. 371 of PCT/US2011/067538, filed Dec. 28, 2011, which claims priority to U.S. Provisional Application No. 61/427,990, filed Dec. 29, 2010, the disclosures of which are incorporated by reference in their entirety herein.

FIELD

The present disclosure relates to an apertured hydrogel. In particular, the present disclosure relates to a dressing with an apertured hydrogel, with a base sheet releasably covering the hydrogel and extending beyond the hydrogel to form a tab.

BACKGROUND

Various tubes, pins, or other percutaneous devices pass through skin for a variety of functions, such as fluid delivery or medical device support. There are several types of percutaneous devices used to administer medication, such as, for example, a diabetic pumps or a Huber needle with an implanted port. Some of these devices may be connected for an extended period of time causing irritation or discomfort on the skin and increasing the risks of infection at the injection site.

SUMMARY

Disclosed is an apertured hydrogel that is used in connection with an insertion device to provide comfort at the site of entry into the skin. In one embodiment, the hydrogel contains antimicrobial properties to help inhibit microbial growth at the site of insertion of the device into the skin. The insertion device is placed adjacent the aperture in the hydrogel. Additionally, a hydrogel can have adhesive properties to help in securing the skin.

In one embodiment, the apertured hydrogel in provided as a medical dressing. The medical dressing comprises a hydrogel having an upper surface and a lower surface, a film covering the upper surface of the hydrogel, a base sheet releasably covering to the lower surface of the hydrogel, an aperture in the film and hydrogel from the upper surface to the lower surface. The base sheet extend beyond the hydrogel to form a tab.

In one embodiment, the hydrogel comprises a main body having an upper surface and a lower surface and an aperture in the main body from the upper surface to the lower surface. The aperture is provided by a retainer.

In one embodiment, the hydrogel is an antimicrobial. In one embodiment, the hydrogel is absorbent. In one embodiment, the hydrogel further comprises a plurality of apertures, wherein each aperture is held open by a retainer. In one embodiment, the retainer is a wall at the aperture forming a through hole in the main body at the aperture. In one embodiment, the retainer is removable from the main body. In one embodiment, removal of the retainer forms a through hole in the main body at the aperture. In one embodiment, the retainer is connected with a base sheet, wherein the base sheet is removable from the main body of the hydrogel to remove the retainer and form a through hole at the aperture in the main body. In one embodiment, the upper surface of the main body is covered with a film. In one embodiment, the main body is covered and surrounded by a dressing having an adhesive border. In one embodiment, a injection device passes through the aperture. In one embodiment, a cover dressing having an adhesive border surrounding a center free of adhesive covers the injection device and secures around the hydrogel.

In one embodiment, a method of creating an apertured hydrogel comprises providing a hydrogel secured to a first sheet and passing a pin through the hydrogel to form an aperture in the hydrogel, wherein the pin is secured to the first sheet and removable from the hydrogel. In one embodiment, the method further comprises removing the first sheet and pin from the hydrogel to create a through hole in the hydrogel at the aperture. In one embodiment, the method further comprises securing the hydrogel to skin and passing an injection mechanism into the through hole and skin. In one embodiment, the method further comprises providing a second sheet secured to the hydrogel. In one embodiment, the second sheet includes an adhesive surface for securing the hydrogel to a surface.

While the above-identified drawings and figures set forth embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of this invention.

The figures may not be drawn to scale.

DETAILED DESCRIPTION

Figure 1:
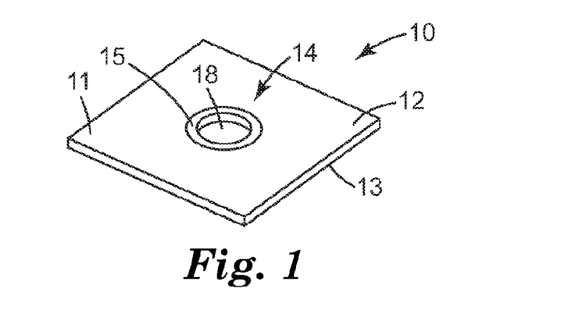
FIG. 1 is a top view of an embodiment of an apertured hydrogel.

FIG. 1 is a top view of an embodiment of an apertured hydrogel 10. The hydrogel 10 comprises a body 11 having an upper surface 12 and a lower surface 13. In use, the lower surface 13 is typically the surface in contact with skin while the upper surface 12 is in contact with an injection mechanism 50 (see FIGS. 7 and 8). The hydrogel body 11 includes at least one aperture 14, which is a discontinuous area within the hydrogel body 11 extending from the upper surface 12 to the lower surface 13. In this embodiment, the aperture 14 is provided by a retainer 15.

Hydrogels can have adhesive properties. Therefore, the lower surface 13 in contact with the skin can aid in providing securement with the skin. Further, depending on the particular application, the upper surface 12, such as shown in FIG. 1, could adhere to the injection mechanism 50. It is understood, that a film, having apertures coinciding with the apertures 14 in the hydrogel 10, could be provided at the upper surface 12 to prevent adhesion between the hydrogel 10 and the injection mechanism 50.

As will be discussed in the various disclosed embodiments, the retainer 15, if included, can be any number of mechanical devices or mechanisms that are capable of providing the aperture 14 in the body 11. The retainer 15 may be provided to create a through hole 18 at the location of the aperture 14. In the embodiment shown in FIG. 1, the retainer 15 is a wall that is not solid in the center and therefore creates a through hole 18 at the location of the aperture 14.

The hydrogel 10 as shown in FIG. 1 could be used by placing directly on prepared skin with an overlying injection mechanism 50. An injection mechanism can be any type of percutaneous device. Typically, the apertured hydrogel 10 is most suitable for providing comfort and in some embodiments antimicrobial effect to injection mechanisms that remain in place for an extended period of time, such as, for example, diabetic pumps, Huber needles, orthopedic supports. The injection device 50 typically has a portion 52 that enters the skin and a portion 53 that remains outside the body. In one embodiment, a needle 52 enters the skin 60 and a hub 53 remains outside the body. The needle 52 of the injection mechanism 50 can pass through the aperture 14 and into the skin 60. It is understood that the hydrogel 10 could be further secured to the skin 60 with tape or an overlying dressing, such as shown in FIGS. 2-5 and 7-8.

Figure 8:
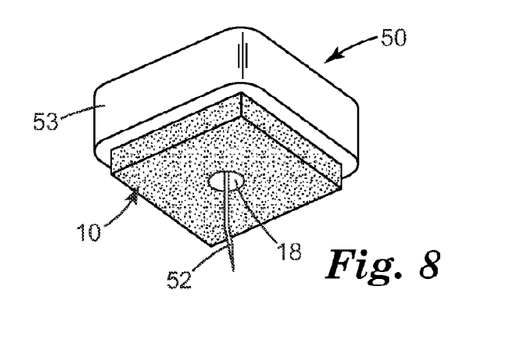
FIG. 8 is a perspective view of an injection mechanism with an apertured hydrogel.

The hydrogel 10 as shown in FIG. 1 could be used directly in combination with the injection mechanism 50 such as shown in FIG. 8. In such an embodiment, the hydrogel 10 could be integrally connected with hub 53 supporting the needle 52 of the injection mechanism 50.

Figure 2:
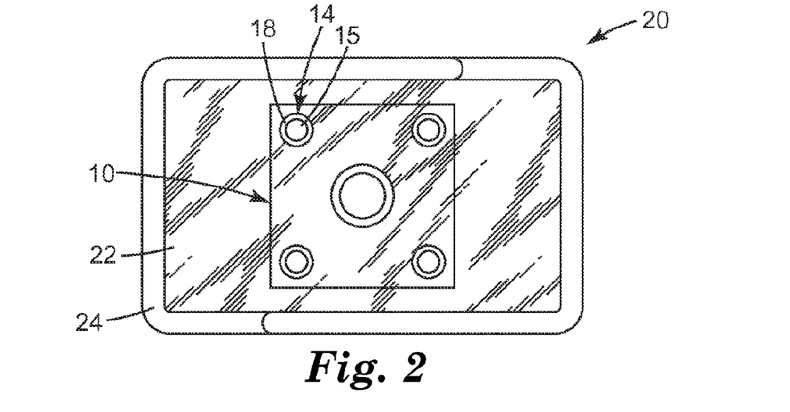
FIG. 2 is a top view of an embodiment of an apertured hydrogel having a gel dressing.

FIG. 2 is a top view of an embodiment of an apertured hydrogel 10 having a gel dressing 20. In this embodiment the apertured hydrogel 10 includes a plurality of apertures 14 provided by retainers 15 at each aperture. In this embodiment, five apertures 14 each having a retainer 15 is shown. As depicted in FIG. 2, the apertures 14 can be of various sizes and it is understood that although the apertures 14 are shown circular, the apertures can be of any size or shape. Also, similar to the embodiment shown in FIG. 1, in this embodiment each retainer 15 is a wall that is not solid in the center and therefore creates a through hole 18 at the location of each aperture 14. In use, a needle 52 of an injection mechanism 50 can pass through the through hole 18 and into the skin 60.

In the embodiment in FIG. 2, the upper surface of the hydrogel 10 secures to a gel dressing 20. The gel dressing 20 includes a film 22 with an adhesive surface that can face the skin of the user to provide securement of the hydrogel 10 to the skin. In one embodiment, the film 22 may be adhesive free on the surface in contact with the hydrogel 10. The film 22 can prevent the upper surface of the hydrogel 10 from adhering to the injection mechanism 50. In one embodiment, the film 22 may include an adhesive on the upper surface to aid in securing the injection mechanism 50. In one embodiment, the film 22 is a thin, transparent, and permeable film and includes a frame 24 to provide structural support during application. To further aid in high permeability of the gel dressing 20 the adhesive may be applied in a discontinuous pattern, such as disclosed in US patent application publication 2008-0233348, herein incorporated by reference. After application to skin 60, the frame 24 can be removed from the film 22. In one embodiment, the film 22 includes apertures coinciding with the apertures 14 of the hydrogel 10.

The hydrogel 10 as shown in FIG. 2 could be used by placing the hydrogel containing gel dressing 20 directly on prepared skin with an overlying injection mechanism 50. The needle 52 of the injection mechanism 50 can pass through the through hole 18 and into the skin 60.

Figure 3:
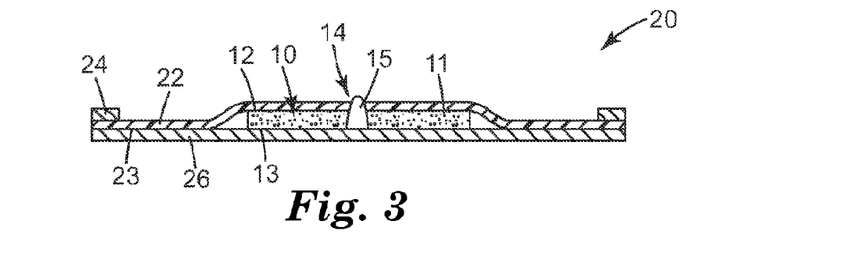
FIG. 3 is a side sectional view of an embodiment of an apertured hydrogel.
Figure 4:
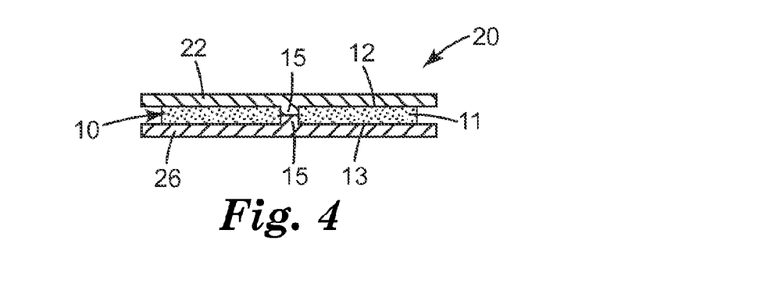
FIG. 4 is a side sectional view of an embodiment of an apertured hydrogel.
Figure 5:
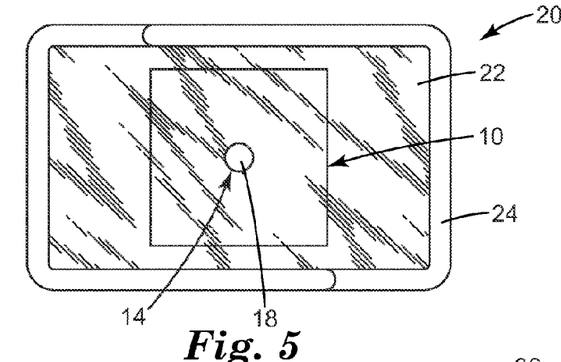
FIG. 5 is a top view of the embodiment of the apertured hydrogel of FIG. 3 with the pin removed creating a through hole.

FIGS. 1 and 2 show embodiments where the retainer 15 is a fixed mechanism that generally stays in place in the body 11 of the hydrogel 10 while the injection mechanism 50 is placed in contact with the hydrogel 10. FIGS. 3-5 show embodiments where the retainer 15 is removable from the body 11 of the hydrogel 10 and would not be place while the injection mechanism 50 is placed in contact with the hydrogel 10.

FIG. 3 is a side view of an embodiment of an apertured hydrogel 10. Similar to FIG. 2, the hydrogel 10 includes a gel dressing 20. In this embodiment the apertured hydrogel 10 includes an aperture 14 provided by a retainer 15.

In the embodiment in FIG. 3, the upper surface 12 of the hydrogel 10 is shown secured to a gel dressing 20. The gel dressing 20 includes a film 22 with an adhesive surface 23 that can face the skin 60 of the user to provide securement of the hydrogel 10. In this embodiment, the gel dressing 20 includes a frame 24 to provide structural support during application of the dressing. A base sheet 26 is included on the lower surface 13 of the hydrogel 10. In this embodiment, the retainer 15 is a pin attached to and extending from the base sheet 26. As shown, the retainer 15 passed through the body 11 of the hydrogel 10 as well as the film 22 of the gel dressing 20. It is understood that the retainer 15 may pass only through the body and not through the film 22 of the gel dressing 20. The base sheet 26 includes a release material to allow it to be releasable connected to the hydrogel 10 and the adhesive surface 23 of the film 22.

FIG. 3 shows a gel dressing 20 that includes film 22 extending beyond the hydrogel 10. It is understood that in some embodiments, a film may be provided only on the upper surface 12 of the hydrogel 10 and a base sheet only on the lower surface 13.

FIG. 4 is a side view of an embodiment of an apertured hydrogel 10. In this embodiment, instead of an entire gel dressing 20, only a film 22 at the upper surface 12 of the body 11 is included. A base sheet 26 at the lower surface 13 of the body 11 is included. The hydrogel 10 can be slightly recessed from either or both the film 22 or base sheet 26 to provide an extending tab to aid in removal of the sheet. A retainer 15 extends from both the base sheet 26 and the film 22 partially into the hydrogel body 11. In this embodiment, at least the base sheet 26 is removable from the hydrogel body 11. Also, the retainers 15 may be solid bodies or may include an opening to provide the through hole 18 through which the needle 52 of the injection mechanism 50 passes. Therefore, for this embodiment, the film 22 could be removable to provide the through hole 18, or in one embodiment the film 22 may remain on the hydrogel 10 with the retainer 15 remaining and providing a through hole 18, For the embodiments shown in FIGS. 3 and 4 depending on the application needs, the film 22 may be removable from the hydrogel 10 and/or the base sheet 26 may be removable from the hydrogel 10. Also, either the film 22 or the base sheet 26 or both may include apertures coinciding with the aperture in the hydrogel 10. It is understood that the retainer 15 may pass only through the body and not through the film 22 of the gel dressing 20. The retainer 15 may be separately secured to the base sheet 26 or may be integrally formed into the base sheet 26.

To use the apertured hydrogel 10 shown in FIGS. 3 and 4, the base sheet 26 is removed from the lower surface 13 of the body 11 thereby removing the retainer 15 from the aperture 14 in the body 11 leaving a through hole 18. Then the exposed lower surface 13 of the body 11 can be secured to skin. FIG. 5 is a top view of the embodiment of the apertured hydrogel of FIG. 3 with the pin removed creating a through hole 18. The needle 52 of the injection mechanism 50 could pass through the through hole 18 and into the skin 60. In this embodiment, where the retainer 15 has been completely removed for the final assembly, the flow of the hydrogel could then migrate over time to be adjacent the inserted needle 52. When an antimicrobial agent is used in the hydrogel, effective antimicrobial protection could be provided at the insertion site to the skin.

Shown and described in the various embodiments, the apertured hydrogel can be placed between skin and an injection mechanism 50. The apertured hydrogel can provide a resilient body for comfort adjacent the skin. In embodiments where the hydrogel is antimicrobial, the hydrogel can also provide antimicrobial properties at the injection site. Various devices, such as, for example, tapes or dressings could be used overlying the injection mechanism to secure the injection mechanism 50 to the skin 60.

Figure 9:
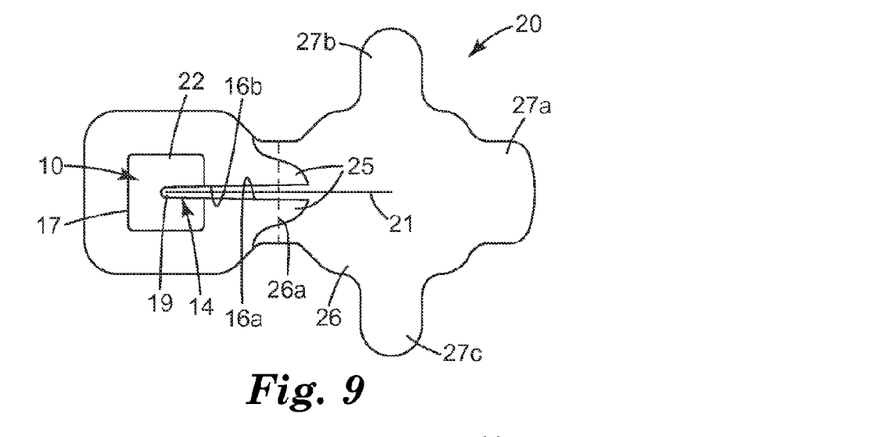
FIG. 9 is a top view of an embodiment of a medical dressing containing an apertured hydrogel.
Figure 10:
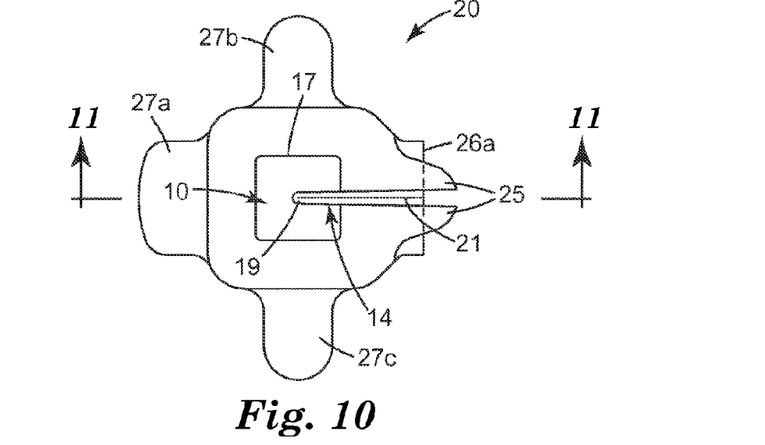
FIG. 10 is a top view of the embodiment of FIG. 9 with the base sheet folded under the medical dressing.
Figure 11:
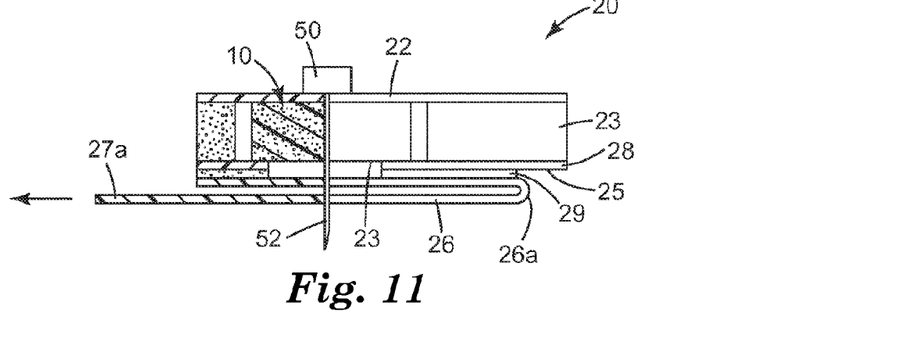
FIG. 11 is a side sectional view of the medical dressing of FIG. 9.

FIGS. 9-11 show an alternative embodiment of an apertured hydrogel 10. In this embodiment, the aperture 14 is a slit 19 from the perimeter 17 of the hydrogel 10 into the body 11 of the hydrogel 10. The slit 19 includes side walls 16a and 16b. In the previous embodiments, the aperture 14 is surrounded entirely by hydrogel 10. In the embodiment shown in FIGS. 9-11, the aperture 14 is not entirely surrounded by hydrogel 10. With this embodiment, where the aperture 14 is a slit 19, the side walls 16a and 16b could be brought into contact with one another such that the aperture 14 is essentially entirely surrounded by hydrogel 10. The hydrogel 10 can provide a stabilizing and cushioning surface, absorption, and in some embodiment antimicrobial efficacy. Therefore, it is desirable to have the aperture 14 surrounded by hydrogel 10.

It is understood that the insertion device (FIG. 11) would be placed within the slit 19 of the hydrogel 10. The slit 19 may be in the shape of an essentially linear passage in to the body of the hydrogel 10 or may be in a triangular, or wedge shape. It is understood that the slit 19 should be of sufficient width to easily allow passage of an insertion needle 52 fully into the slit 19. In one embodiment, once the insertion needle 52 is placed though the slit 19, the side walls 16a, 16b may be manipulated to be placed nearer one another to be nearly or entirely surrounding the insertion needle 52 with hydrogel 10.

If the side walls 16a, 16b come in contact with one another, the hydrogel 10 may stick to itself. The side walls 16a and 16b may be deadened, chemically or mechanically to prevent resticking. For example, sidewalls 16a and 16b could be detackified or a film may be placed over the sidewalls 16a, 16b.

Although the apertured hydrogel 10 in FIGS. 9-11 is shown placed in combination with a gel dressing 20 (discussed below) it is understood that similar to previously described embodiment, the apertured hydrogel 10 may be provided with or without an gel dressing 20 or directly applied to a medical device. Although not shown, a retainer 15 (similar to described previously) may be incorporated into the hydrogel 10 to maintain the aperture 14, in this embodiment the slit 19.

In this embodiment in FIGS. 9-11 the apertured hydrogel 10 is incorporated into a gel dressing 20. The gel dressing 20 includes a film 22 at the upper surface 12 of the hydrogel 10. Typically the film 22 includes an adhesive 23. In this embodiment, the adhesive 23 generally surrounds the hydrogel 10 but does not cover the hydrogel 10 to allow for better moisture permeability out of the hydrogel 10 and film 22. It is understood, that this adhesive 23 may be the adhesive to stick the dressing to skin 60. However, in this embodiment, and additional support film 28 with an adhesive 29 is included at a lower surface 13 of the hydrogel 10. This support film 28 generally surrounds the hydrogel 10 but does not entirely cover the hydrogel 10 such that a portion of the hydrogel 10 would contact skin 60. In this embodiment, the film 22 and support film 28, wherein the support film 28 covers a portion of the lower surface 13 of the hydrogel 10, hold in the hydrogel 10 within the gel dressing 20. This construction, see FIG. 11, is desirable because during removal, the hydrogel 10 is more likely to remove with the entire gel dressing 20. Also, as can be seen the thickness of the various layers of film and/or adhesive can be manipulated to compensate for the thickness of the hydrogel 10.

In the embodiment shown in FIGS. 9-11, the film 22 of the gel dressing 20 includes adhesive-free extensions 25 extending outward from each of the sides of the slit 19. These extensions 25 provide an adhesive free area that will aid in removal of the gel dressing 20 from skin 60 but also aid in allowing for manipulation of the extent to which the slit 19 is opened or closed in around the insertion device 50.

A base sheet 26 is included that covers the lower surface 13 of the hydrogel 10 and in this embodiment the adhesive 29 of the support film 28. The base sheet 26 includes a tab 27a that extends beyond the perimeter 17 of the hydrogel 10, more specifically, extends beyond the film 22 and support film 28. The base sheet 26 typically does not include adhesive and therefore the tab 27a aids in removing the base sheet 26 from the hydrogel 10.

In the embodiment shown in FIGS. 9-11, the base sheet 26 covers the hydrogel 10, includes a fold 26a, and the tab 27a extends beyond the hydrogel 10 perimeter 17. In this embodiment, additional tabs 27b and 27c are also included. Also included in the base sheet 26 is a cut 21. Cut 21 is a through cut in the base sheet 26 that coincides with the slit 19. Cut 21 along with the slit 19 allow for the insertion needle 52 to enter into the aperture 14. Tabs 27b and 27c, which are adhesive free, if included could be used to hold the gel dressing 20 with injection mechanism 50 in place (FIG. 11) for placement over skin 60. Once needle 52 is inserted, the base sheet 26 can be pulled by the tab 27a in the direction of the arrow shown in FIG. 11. Because of the cut 21 in the base sheet 26, the base sheet 26 freely passes by the insertion needle 52, and the base sheet 26 is entirely removed from the lower surface 13 of the hydrogel 10. The hydrogel 10 and gel dressing 20 are then in contact with the skin with the needle 52 inserted.

In some instances the insertion device 50 may be in place over the skin and removal of the insertion device is undesirable. In that case, the apertured hydrogel 10 may be slid under the hub 53 and with needle 52 in the aperture. In the embodiments where the apertured hydrogel 10 is incorporated with a gel dressing 20 such as shown in FIGS. 9-11, the gel dressing 20 is slid under the hub 53 and the needle 52 is placed in the aperture 14 and cut 21 of the base sheet 26.

Once in place, the base sheet 26 can be pulled by the tab 27a in the direction of the arrow shown in FIG. 11. Because of the cut 21 in the base sheet 26, the base sheet 26 freely passes by the insertion needle 52, and the base sheet 26 is entirely removed from the lower surface 13 of the hydrogel 10. The hydrogel 10 and gel dressing 20 are then in contact with the skin with the needle 52 inserted. As with other embodiments, a cover dressing 30 could be applied over the whole assembly. As with other embodiment, a removable frame 24 may be included to provide structural support to the gel dressing 20.

It is understood that the various films or sheets included in a gel dressing 20 can be single layer film or multilayer composites. If a multilayer composition the multilayer portion may be over the entire gel dressing or just a portion that is a multilayer composite. For example, in the embodiment shown in FIGS. 9-11, film 22 may be a thin, transparent film, but at the outer border may include a foam, woven, nonwoven, or knitted material for structural support of the film 22.

It is understood that the film 22 may include adhesive on both surfaces, such that the adhesive at the surface opposite adhesive 23 enables securement to the injection mechanism 50.

Figure 6:
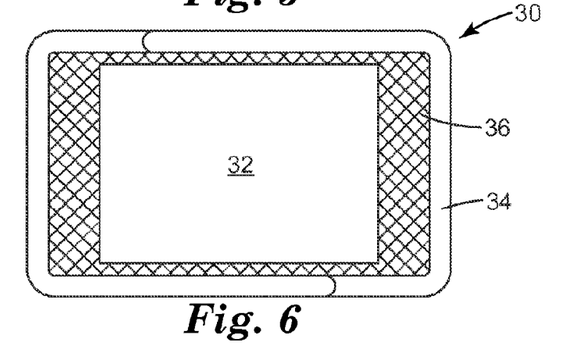
FIG. 6 is a top view of an embodiment of a cover dressing.

FIG. 6 is a top view of an embodiment of a cover dressing 30 that would be suitable for securing the injection mechanism 50 to the skin 60. The cover dressing 30 includes a film 32 having an adhesive surface 36 for contacting the skin 60. In this embodiment, the adhesive 36 is at a perimeter of the dressing 30 while the center of the dressing 30 is essentially free of adhesive. The adhesive-free area provides the advantage that the dressing does not readily stick to the underlying injection assembly 50 and instead sticks to the surrounding skin 60. Also, in embodiment where the hydrogel 10 is provided with a gel dressing 10, it would be desirable for the cover dressing 30 adhesive free portion to extend over the entire area of the gel dressing 10. In one embodiment, the film 32 is a thin, transparent, and permeable film and therefore typically includes a frame 34 to provide structural support during application. The film 32 may include single or multilayers. After application to skin 60, the frame 34 can be removed from the film 32. To further aid in high permeability of the cover dressing 30 the adhesive 36 may be applied in a discontinuous pattern, such as disclosed in US patent application publication 2008-0233348, the disclosure of which is herein incorporated by reference. In addition, the cover dressing 30 may included a notched portion to allow for the attached tubing of the injection mechanism to pass through and secure. Such notched portions are included on products such as 3M Tegaderm™ IV dressing available from 3M Company, St. Paul, Minn.

Figure 7:
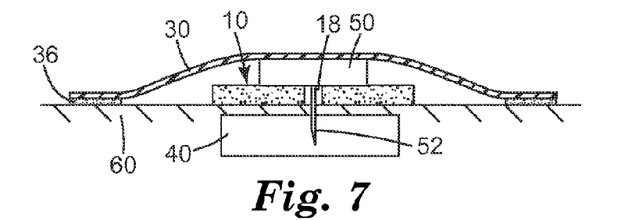
FIG. 7 is a side sectional view of an embodiment of an apertured hydrogel, injection mechanism, and cover dressing

FIG. 7 is a side view of an embodiment of an apertured hydrogel 10, injection mechanism 50, and cover dressing 30. As shown, a port 40 is inserted under the skin 60. Positioned between the skin 60 and the injection mechanism 50 is the apertured hydrogel 10. The apertured hydrogel may include the optional gel dressing 20 as described in FIG. 2. The apertured hydrogel in this embodiment has the retainer removed to create the through hole 18 through which the needle 52 of the injection mechanism 50 passes. It is understood that the apertured hydrogel could include a retainer as well as the through hole 18. Overlying the injection mechanism is the cover dressing 30. The cover dressing 30 secures to the surrounding skin 60 and provides tension to secure the injection mechanism 50 from movement while inserted into the skin.

A hydrogel is a cross-linked polymer gel. Hydrogels are typically very flexible. Hydrogels provide and maintain a moist environment at the contact point on skin by increasing moisture content. Generally, hydrogels can be removed without trauma to the wound. Common ingredients are for example polyvinyl alcohol, sodium polyacrylate, acrylate polymers and copolymers with hydrophilic groups. A commercially available example of a hydrogel are Flexigel Hydrogel Sheet available from Smith & Nephew, Tegaderm CHG dressing available from 3M Company, St. Paul, Minn.

Hydrocolloids are similar to hydrogels but have the ability to absorb moisture. It is understood that for purposes of this disclosure a hydrogel or a hydrocolloid may be used. Hydrocolloids typically comprise a blend of a polymer matrix, such as a rubbery elastomer like polyisobutylene, in combination with one or more water-soluble or water-swellable hydrocolloids, such as a dry powdered mixture of pectin, gelatin and carboxymethylcellulose. Upon absorption of a liquid the hydrocolloid form a gel-like substance.

Hydrogels and hydrocolloids that have absorbed liquid can be somewhat flowable. In some instances, if the hydrogel 10 is desired to be used repeatedly including a retainer 15 that remains in the body 11 to hold open the through hole 18 may be desirable. In such an instance, the needle 52 can be inserted through the through hole 18 repeatedly without removal of the hydrogel 10 and optionally attached gel dressing 20. To aid in the repeated use of the hydrogel 10, a film could be included at the upper surface 12 of the body 10 to prevent the hydrogel 10 from sticking to the injection mechanism 50. The film could be similar to that shown in FIG. 2, however in FIG. 2 the film extends beyond and around the hydrogel 10 to provide additional securement.

In some instances, the hydrogel 10 may be used for one insertion of the needle 52 through a particular through hole 18. Therefore, in such instances, use of a retainer 15 that is removable from the body 11 to create the through hole 18 through which the needle 52 may be inserted. Over time, the body 11 at the site of the aperture 14 may flow in an around the needle 52.

As discussed previously, the hydrogel may contain an antimicrobial or antiseptic agent to deliver an antimicrobial agent to the skin in and around the injection site, reducing the likeliness of an infection or to treat infections of the skin or wounds.

There are numerous biologically active materials, which include antimicrobial agents. Examples of antimicrobial agents include Parachlorometaxylenol; triclosan; Chlorhexidine and its salts such as Chlorhexidine Gluconate, poly hexamethylene biguanide and its salts such as poly hexamethylene biguanidine chloride, iodine, idodophors; fatty acid monoesters; poly-n-vinyl pyrrolidone-iodophors; silver oxide, silver and its salts, peroxides (e.g. hydrogen peroxide), antibiotics (e.g. neomycin, bacitracin, and polymixin B).

The following active ingredients could also be used to suppress the regrowth or possibly treat an infection of microorganisms in the present invention: 2,2-thiobis(4-chlorophenol); 4,4-isopropylidenediphenol; 5-amino-6-chloro-o-cresol; acetaminosalol; alcloxa; aldioxa; aluminum acetate; aluminum benzoate; aluminum diacetate; aluminum formate; aluminum phenolsulfonate; ammonium iodide; ammonium phenolsulfonate; benzisothiazolinone; benzotriazole; benzoxiquine; benzylparaben; berberine chloride; boric acid; cetethyl morpholinium ethosulfate; cetethyldimonium bromide; cetrimonium tosylate; cetylpyridinium chloride; chloramine-t; chlorothymol; cloflucarban; cocotrimonium chloride; colloidal sulfur; copper usnate; dedm hydantoin; dedm hydantoin dilaurate; dequalinium acetate; dequalinium chloride; dibromopropamidine diisethionate;

dichloro-m-xylenol; dichlorophene; dichlorophenyl imidazoldioxolan; diiodomethyltolylsulfone; dimethyl hydroxymethyl pyrazole; dimethylaminostyryl heptyl methyl thiazolium iodide; dodecylbenzyltrimonium chloride; domiphen bromide; ferulic acid; fluorosalan; glyoxal; hydroxymethyl dioxoazabicyclooctane; hydroxypropyl bistrimonium diiodide; ichthammol; isodecylparaben; isopropyl sorbate; lapyrium chloride; laurtrimonium trichlorophenoxide; lauryl isoquinolinium bromide; lauryl isoquinolinium saccharinate; laurylpyridinium chloride; m-cresol; mandelic acid; MDM hydantoin; MEAa-iodine; melaleuca alternifolia; methylbenzethonium chloride; mixed cresols; nonoxynol-12 iodine; nonoxynol-9 iodine; o-cresol; oxyquinoline benzoate; oxyquinoline sulfate; p-chlorophenol; p-cresol; PEG-15 dedm hydantoin; PEG-15 dedm hydantoin stearate; PEG-5 dedm hydantoin; PEG-5 dedm hydantoin oleate; phenol; phenoxyethylparaben; phenyl salicylate; polymethoxy bicyclic oxazolidine; potassium iodide; potassium lactate; potassium phenoxide; potassium troclosene; quaternium-14; quaternium-24; quaternium-8; ricinoleamidopropyltrimonium methosulfate; sodium iodide; sodium p-chloro-m-cresol; sodium phenolsulfonate; sodium phenoxide; sodium usnate; steapyrium chloride; strontium peroxide; teasorbate; tetrabutyl ammonium bromide; thiabendazole; triacetin; undecylenamide dea; undecylenamide mea; undecylenamidopropyltrimonium methosulfate; undecyleneth-6; undecylenoyl peg-5 paraben; usnic acid; zinc acetate; zinc borate; zinc phenolsulfonate; zinc sulfate; zinc undecylenate; and combinations of the foregoing.

The following actives could also be of use to also reduce regrowth of microorganisms on skin: 2-bromo-2-nitropropane-1,3-diol; 4-hydroxybenzoic acid; 5-bromo-5-nitro-1,3-dioxane; 7-ethylbicyclooxazolidine; ammonium benzoate; ammonium bisulfite; ammonium propionate; ammonium sulfite; behentrimonium chloride; benzalkonium bromide; benzalkonium chloride; benzalkonium saccharinate; benzethonium chloride; benzoic acid; benzyl alcohol; benzylhemiformal; bromochlorophene; butyl benzoate; butylparaben; calcium benzoate; calcium paraben; calcium propionate; calcium salicylate; calcium sorbate; calcium undecylenate; cetalkonium chloride; cetearalkonium bromide; cetrimonium bromide; cetrimonium chloride; chloroacetamide; chlorobutanol; chlorophene; chloroxylenol; chlorphenesin; climbazole; dehydroacetic acid; diazolidinyl urea; dibromohexamidine isethionate; dichlorobenzyl alcohol; dimethyl oxazolidine; DMDM hydantoin; ethyl benzoate; ethylparaben; formaldehyde; formic acid; glutaral; hexamidine; hexamidine diisethionate; hexamidine paraben; hexetidine; hydrogenated tallowtrimonium chloride; imidazolidinyl urea; iodopropynyl butylcarbamate; isobutyl benzoate; isobutylparaben; isopropyl benzoate; isopropyl cresols; isopropylparaben; lauralkonium bromide; lauralkonium chloride; laurtrimonium bromide; laurtrimonium chloride; magnesium benzoate; magnesium propionate; magnesium salicylate; MEA o-phenylphenate; MEA-benzoate; MEA-salicylate; MEA-undecylenate; methenamine; methyl benzoate; methylchloroisothiazolinone; methyldibromo glutaronitrile; methylisothiazolinone; methylparaben; myristalkonium chloride; myristalkonium saccharinate; myrtrimonium bromide; o-cymen-5-ol; o-phenylphenol; olealkonium chloride; p-chloro-m-cresol; phenoxyethanol; phenoxyisopropanol; phenyl benzoate; phenyl mercuric acetate; phenyl mercuric benzoate; phenyl mercuric borate; phenyl mercuric bromide; phenyl mercuric chloride; phenylparaben; piroctone olamine; polyaminopropyl biguanide; potassium benzoate; potassium butylparaben; potassium ethylparaben; potassium metabisulfite; potassium methylparaben; potassium o-phenylphenate; potassium paraben; potassium propionate; potassium propylparaben; potassium salicylate; potassium sorbate; potassium sulfite; propionic acid; propyl benzoate; propylparaben; quaternium-15; salicylic acid; sodium benzoate; sodium bisulfite; sodium butylparaben; sodium dehydroacetate; sodium ethylparaben; sodium formate; sodium hydroxymethylglycinate; sodium iodate; sodium metabisulfite; sodium methylparaben; sodium o-phenylphenate; sodium paraben; sodium propionate; sodium propylparaben; sodium salicylate; sodium sorbate; sodium sulfite; sodium undecylenate; sorbic acid; soytrimonium chloride; stearalkonium chloride; steartrimonium chloride; tallowalkonium chloride; tallowtrimonium chloride; thimerosal; triclocarban; triclosan; undecylenic acid; zinc pyrithione; and combinations of the foregoing.

US Patent application publications 2004-0247655 and 2004-0247654, the disclosure of which are herein incorporated by reference disclose adhesive compositions and antimicrobial agents used therein. For example, chlorohexidine gluconate can be included within the gel to provide continuous antimicrobial activity. A commercially available antimicrobial hydrogel is a 3M™ Tegaderm™ CHG dressing (a product of 3M Company, St. Paul, Minn.)

The retainer 15, if included, can be formed of any material that will create an aperture 14 in the body 11 of the hydrogel. The retainer 15 may be a polymeric material, metal, foam, sponge, or film. The retainer 15 that remains in with the body 11 while the needle 52 is inserted, the retainer may be a resilient material, such as a foam or elastomeric polymeric material, to aid in providing comfort at the needle 52 insertion site. The retainer 15, if a solid body at the aperture 14, may be of a material that allows for a needle 52 to pass through.

The gel dressing 20 and cover dressing 30 in combination with the adhesive could have high moisture vapor permeability. One example of a suitable material is a high moisture vapor permeable film such as described in U.S. Pat. Nos. 3,645,835 and 4,595,001, the disclosures of which are herein incorporated by reference. Issued U.S. Pat. Nos. 3,645,835 and 4,595,001, the disclosures of which are hereby incorporated by reference, describe methods of making such films and methods for testing their permeability. Preferably, the film/adhesive composite should transmit moisture vapor at a rate equal to or greater than human skin. Preferably, the adhesive coated film transmits moisture vapor at a rate of at least 300 g/m$^2$/24 hrs/37° C./100-10% RH, more preferably at least 700 g/m$^2$/24 hrs/37° C./100-10% RH, and most preferably at least 2000 g/m$^2$/24 hrs/37° C./100-10% RH using the inverted cup method as described in U.S. Pat. No. 4,595,001.

The film 22, 32, 28 of the dressing is preferably conformable to anatomical surfaces. As such, when applied to an anatomical surface, it conforms to the surface even when the surface is moved and can stretch and retract. One embodiment of a film is elastomeric polyurethane, polyester, or polyether block amide films. These films combine the desirable properties of resiliency, high moisture vapor permeability, and transparency. Typically, thin film dressing includes a frame 24. The frame is made of a substrate that is less resilient than the film and may be removable from the film.

The adhesive used on the film typically is a pressure sensitive adhesive, and adhesives that can be applied to skin such as the acrylate copolymers described in U.S. Pat. No. RE 24,906, the disclosure of which is hereby incorporated by reference. In one embodiment, a 97:3 iso-octyl acrylate:acrylamide copolymer adhesive can be used or a 70:15:15 isooctyl acrylate: ethyleneoxide acrylate:acrylic acid terpolymer, as described in U.S. Pat. No. 4,737,410 (Example 31), the disclosure of which is hereby incorporated by reference. Other useful adhesives are described in U.S. Pat. Nos. 3,389,827, 4,112,213, 4,310,509, and 4,323,557, the disclosures of which are hereby incorporated by reference. Inclusion of medicaments or antimicrobial agents in the adhesive is also contemplated, as described in U.S. Pat. Nos. 4,310,509 and 4,323,557 both of which are hereby incorporated by reference.

Silicone adhesive can also be used. Generally, silicone adhesives can provide suitable adhesion to skin while gently removing from skin. Suitable silicone adhesives are disclosed in PCT Publications WO2010/056541 and WO2010/056543, the disclosure of which are herein incorporate by reference.

The pressure sensitive adhesives described above typically transmit moisture vapor at a rate greater to or equal to that of human skin. While such a characteristic can be achieved through the selection of an appropriate adhesive, it is also contemplated in the present invention that other methods of achieving a high relative rate of moisture vapor transmission may be used, such as pattern coating the adhesive on the backing, as described in U.S. Pat. No. 4,595,001 which is hereby incorporated by reference. Also, it is understood that the entire surface of the film may include adhesive or the adhesive may be on select portions of the film. Therefore, the adhesive could be applied in selection regions of the film in a continuous or discontinuous manner.

Release liners (i.e., the base sheet) maybe used with the gel dressing 20 and cover dressing 30 to removably cover the adhesive containing surface. Release liners can be made of kraft papers, polyethylene, polypropylene, polyester or composites of any of these materials. The liners are preferably coated with release agents such as fluorochemicals or silicones. For example, U.S. Pat. No. 4,472,480, the disclosure of which is hereby incorporated by reference, describes low surface energy perfluorochemical liners. Suitable liners are papers, polyolefin films, or polyester films coated with silicone release materials. Examples of commercially available silicone coated release papers are POLYSLIK™ silicone release papers available from James River Co., H. P. Smith Division (Bedford Park, Ill.) and silicone release papers supplied by Daubert Chemical Co. (Dixon, Ill.). One example of a liner is 1-603KG-157 paper liner available from Daubert, which is a super calendared Kraft paper with a water-based silicone release surface.

Although specific embodiments of this invention have been shown and described herein, it is understood that these embodiments are merely illustrative of the many possible specific arrangements that can be devised in application of the principles of the invention. Numerous and varied other arrangements can be devised in accordance with these principles by those of ordinary skill in the art without departing from the spirit and scope of the invention. Thus, the scope of the present invention should not be limited to the structures described in this application, but only by the structures described by the language of the claims and the equivalents of those structures.

What is claimed is:

1. A medical dressing comprising:
   a hydrogel having an upper surface and a lower surface;
   a first film covering the upper surface of the hydrogel;
   an aperture in the first film and hydrogel from the upper surface to the lower surface of the hydrogel, wherein the aperture is a slit into the hydrogel from a perimeter of the hydrogel;
   a base sheet releasably covering the lower surface of the hydrogel, wherein a first portion of the base sheet extends beyond the perimeter of the hydrogel and is folded back at a fold onto a second portion of the base sheet covering the lower surface of the hydrogel such that the base sheet extends beyond the perimeter of the hydrogel opposite the fold to form a first tab; and
   a continuous cut which passes through the fold of the base sheet but does not extend to the perimeter of the base sheet, wherein the continuous cut coincides with the aperture in the first film and hydrogel;
   wherein the first portion of the base sheet comprises second and third tabs that extend beyond the perimeter of the hydrogel in opposite directions.

2. The medical dressing of claim 1, wherein the aperture is defined by side walls, and wherein the hydrogel exposed at the side walls is altered to prevent resticking.

3. The medical dressing of claim 2, wherein the hydrogel exposed at the side walls is detackified.

4. The medical dressing of claim 1, wherein a portion of the first film extends beyond the perimeter of the hydrogel.

5. The medical dressing of claim 4, wherein the first film over the hydrogel is free of adhesive and the portion of the first film extending beyond the perimeter of the hydrogel comprises an adhesive.

6. The medical dressing of claim 1, further comprising a support film between the first film and the second portion of the base sheet, the support film surrounding the hydrogel and extending inward to cover only a portion of the lower surface of the hydrogel.

7. The medical dressing of claim 1, wherein the slit is wedge shape.

* * * * *

UNITED STATES PATENT AND TRADEMARK OFFICE
CERTIFICATE OF CORRECTION

PATENT NO. : 9,572,942 B2  
APPLICATION NO. : 13/995232  
DATED : February 21, 2017  
INVENTOR(S) : Deena Conrad-Vlasak et al.

Page 1 of 1

It is certified that error appears in the above-identified patent and that said Letters Patent is hereby corrected as shown below:

In the Specification

Column 2  
Line 35, delete "hole." and insert -- hole; --, therefor.  
Line 39-40, after "dressing" insert -- ; --.  
Line 46, after "dressing;" insert -- and --.

Column 4  
Line 63, delete "18," and insert -- 18. --, therefor.

Column 8  
Line 48, delete "idodophors;" and insert -- iodophors; --, therefor.  
Line 51, delete "polymixin" and insert -- polymyxin --, therefor.

Column 9  
Line 23, delete "teasorbate;" and insert -- tea-sorbate; --, therefor.

Column 11  
Line 46, delete "1-603KG-157" and insert -- 1-60BKG-157 --, therefor.

Signed and Sealed this  
Seventh Day of November, 2017

Joseph Matal  
*Performing the Functions and Duties of the  
Under Secretary of Commerce for Intellectual Property and  
Director of the United States Patent and Trademark Office*